(12) United States Patent
Chang et al.

(10) Patent No.: US 7,026,267 B2
(45) Date of Patent: Apr. 11, 2006

(54) MOLECULAR SIEVE CATALYST COMPOSITION, ITS PRODUCTION AND USE IN CONVERSION PROCESSES

(75) Inventors: Yun-Feng Chang, Houston, TX (US); Stephen N. Vaughn, Kingwood, TX (US); Luc Roger Marc Martens, Meise (BE); Jeffrey Wayne Sprinkle, Baytown, TX (US); Ian Nathaniel Walker, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/325,281

(22) Filed: Dec. 20, 2002

(65) Prior Publication Data

US 2004/0121902 A1 Jun. 24, 2004

(51) Int. Cl.
*B01J 29/06* (2006.01)

(52) U.S. Cl. ........................ 502/214; 502/208
(58) Field of Classification Search ........... 502/208, 502/214
See application file for complete search history.

(56) References Cited

U.S. PATENT DOCUMENTS

| | | | |
|---|---|---|---|
| 4,062,905 A | 12/1977 | Chang et al. ........... 260/682 |
| 4,079,095 A | 3/1978 | Givens et al. ........... 260/682 |
| 4,310,440 A | 1/1982 | Wilson et al. ........... 252/435 |
| 4,440,871 A | 4/1984 | Lok et al. ........... 502/214 |
| 4,499,327 A | 2/1985 | Kaiser ........... 585/640 |
| 4,677,242 A | 6/1987 | Kaiser ........... 585/638 |
| 4,677,243 A | 6/1987 | Kaiser ........... 585/638 |
| 4,873,390 A | 10/1989 | Lewis et al. ........... 585/638 |
| 4,987,110 A | 1/1991 | Scherzer ........... 502/68 |
| 5,095,163 A | 3/1992 | Barger ........... 585/640 |
| 5,110,776 A | 5/1992 | Chitnis et al. ........... 502/64 |
| 5,348,643 A | 9/1994 | Absil et al. |
| 5,367,100 A | 11/1994 | Gongwei et al. ........... 585/640 |
| 5,378,670 A * | 1/1995 | Kumar ........... 502/60 |
| 5,472,922 A | 12/1995 | Degnan et al. |
| 5,714,662 A | 2/1998 | Vora et al. ........... 585/640 |
| 5,925,586 A * | 7/1999 | Sun ........... 502/62 |
| 6,080,303 A * | 6/2000 | Cao et al. ........... 208/120.01 |
| 6,121,503 A | 9/2000 | Janssen et al. |
| 6,153,552 A | 11/2000 | Wachter et al. ........... 502/208 |
| 6,166,282 A | 12/2000 | Miller ........... 585/638 |
| 2002/0049133 A1 | 4/2002 | Ziebarth et al. ........... 502/64 |

FOREIGN PATENT DOCUMENTS

EP 0 933 345 8/1999
WO WO00/63144 10/2000

* cited by examiner

*Primary Examiner*—Christina Johnson

(57) ABSTRACT

The invention relates to a molecular sieve catalyst composition, to a method of making or forming the molecular sieve catalyst composition, and to a conversion process using the catalyst composition. In particular, the invention is directed to a catalyst composition comprising a molecular sieve having a framework including at least $[AlO_4]$ and $[PO_4]$ tetrahedral units, at least one of a binder and a matrix material and at least one phosphorus compound separate from said molecular sieve wherein, after calcination at 760° C. for 3 hours, said catalyst composition has a microporous surface area in excess of 20% of the microporous surface area of said molecular sieve after calcination at 650° C. in nitrogen for 2 hours. The catalyst composition is particularly useful in a conversion process for producing olefin(s), preferably ethylene and/or propylene, from a feedstock, preferably an oxygenate containing feedstock.

27 Claims, No Drawings

US 7,026,267 B2

MOLECULAR SIEVE CATALYST COMPOSITION, ITS PRODUCTION AND USE IN CONVERSION PROCESSES

FIELD

The present invention relates to a molecular sieve catalyst composition, to a method of producing the catalyst composition, and to the use of catalyst composition in conversion processes particularly to produce olefin(s).

BACKGROUND

Olefins are traditionally produced from petroleum feedstocks by catalytic or steam cracking processes. These cracking processes, especially steam cracking, produce light olefin(s) such as ethylene and/or propylene from a variety of hydrocarbon feedstocks. Ethylene and propylene are important commodity petrochemicals useful in a variety of processes for making plastics and other chemical compounds.

The petrochemical industry has known for some time that oxygenates, especially alcohols, are convertible into light olefin(s). The preferred alcohol for light olefin production is methanol and the preferred process for converting a methanol-containing feedstock into light olefin(s), primarily ethylene and/or propylene, involves contacting the feedstock with a molecular sieve catalyst composition.

There are many different types of molecular sieves well known to convert a feedstock, especially an oxygenate containing feedstock, into one or more olefin(s). For example, U.S. Pat. No. 5,367,100 describes the use of the well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; and U.S. Pat. No. 4,310,440 describes producing light olefin(s) from an alcohol using a crystalline aluminophosphate.

One of the most useful molecular sieves for converting methanol to olefin(s) are silicoaluminophosphate molecular sieves. Silicoaluminophosphate (SAPO) molecular sieves contain a three-dimensional microporous crystalline framework structure of $[SiO_2]$, $[AlO_2]$ and $[PO_2]$ corner sharing tetrahedral units. SAPO synthesis is described in U.S. Pat. No. 4,440,871, which is herein fully incorporated by reference. SAPO molecular sieves are generally synthesized by the hydrothermal crystallization of a reaction mixture of silicon-, aluminum- and phosphorus-sources and at least one templating agent. Synthesis of a SAPO molecular sieve, its formulation into a SAPO catalyst, and its use in converting a hydrocarbon feedstock into olefin(s), particularly where the feedstock is methanol, is shown in U.S. Pat. Nos. 4,499,327, 4,677,242, 4,677,243, 4,873,390, 5,095,163, 5,714,662 and 6,166,282, all of which are herein fully incorporated by reference.

When used in the conversion of methanol to olefins, most molecular sieves, including SAPO molecular sieves, undergo rapid coking and hence require frequent regeneration, typically involving exposure of the catalyst to high temperatures and steaming environments. Moreover, these processes are typically conducted in a fluidized bed reactor where the catalyst is continuously circulated between a reaction zone and a regeneration zone. This continuous circulation necessarily results in collisions between the catalyst composition particles themselves and with the reactor walls which can cause the particles to breakdown into smaller particles called fines. This physical breakdown of catalyst particles is known as attrition and is undesirable because the fines often exit the reactor in the effluent stream resulting not only in catalyst losses but also in problems in downstream recovery systems.

There is therefore a need for a molecular sieve catalyst composition which can be used in the conversion of feedstocks, such as oxygenates, to olefins and which exhibits both a high thermal and hydrothermal stability and a high attrition resistance.

U.S. Pat. No. 6,153,552 discloses that the attrition resistance of a SAPO catalyst can be enhanced by the addition of an external phosphorus source in an amount between 0.1 and 25 wt %, preferably between 1 and 20 wt %, of the finished catalyst. The external phosphorus source is typically a phosphate and is added by mixing with the molecular sieve, an inorganic oxide sol and a clay to form a slurry which is then spray dried. However, the Examples show that, after calcination at 760° C. for 3 hours, the attrition resistance of the catalyst decreases significantly and its surface area falls dramatically.

U.S. Pat. No. 5,110,776 discloses a method of preparing a catalytic cracking catalyst comprising treating a zeolite, such as REY, with an aqueous phosphate solution, combining the resultant aqueous mixture with a matrix precursor, such as alumina, and then spray drying the resultant slurry. The catalyst is reported to have improved attrition resistance and octane when used in catalytic cracking.

U.S. Pat. No. 4,987,110 discloses that an attrition resistant catalytic cracking catalyst can be prepared by spray drying a slurry formed by combining a molecular sieve, which can be a zeolite or a SAPO, with a clay, a silica sol and aluminum chlorohydroxide.

U.S. Patent Application Publication No. 2002/0049133 discloses that an attrition resistant catalytic cracking catalyst can be prepared by forming a slurry of a zeolite having a constraint index of 1 to 12, such as ZSM-5, a phosphorus-containing compound and alumina in an amount less than 10 wt % of the slurry and then spray drying and calcining the slurry.

SUMMARY

In one aspect, the present invention resides in a catalyst composition comprising a molecular sieve having a framework including at least $[AlO_4]$ and $[PO_4]$ tetrahedral units, at least one of a binder and a matrix material and at least one phosphorus compound separate from said molecular sieve wherein, after calcination at 760° C. in nitrogen for 3 hours, said catalyst composition has a microporous surface area in excess of 20%, such as in excess of 50%, of the microporous surface area of said molecular sieve after calcination at 650° C. in nitrogen for 2 hours.

Conveniently, said phosphorus compound is present in amount of between about 0.05 and about 15 wt %, for example between about 0.1 and about 10 wt %, such as between greater 1.0 and about 5 wt %, expressed as $P_2O_5$, by weight of the catalyst composition.

In one embodiment, the catalyst composition has an Attrition Rate Index (ARI), of less than 3 wt % per hour, such as less than 0.95 wt % per hour, for example about 0.05 to about 0.8 wt % per hour.

Conveniently, the catalyst composition includes a binder, such as an alumina sol, and a matrix material, such as a clay.

Typically, the molecular sieve is an aluminophosphate or a silicoaluminophosphate.

In another aspect, the invention resides in a catalyst composition comprising a molecular sieve having a framework including at least [AlO$_4$] and [PO$_4$] tetrahedral units, at least one of a binder and a matrix material and at least one phosphorus compound separate from said molecular sieve wherein, after hydrothermal treatment at 800° C. for 18 hours at a water vapor pressure of 45 psig, said catalyst composition retains at least 15% of the methanol conversion activity of the untreated catalyst composition.

In a further aspect, the invention resides in a method for making a catalyst composition, the method comprising (a) forming a slurry comprising a binder or binder precursor and a molecular sieve in a liquid medium, the slurry being substantially free of any phosphorus compounds except as may be present in said molecular sieve;

(b) mixing a phosphorus compound with said slurry to produce a phosphorus-containing mixture;

(c) adding a matrix to the phosphorus-containing mixture to produce a catalyst precursor mixture, (d) spray drying the catalyst precursor mixture to produce particles of said catalyst composition, and then (e) calcining said catalyst composition particles Conveniently, said phosphorus compound is an inorganic phosphorus compound and typically is selected from phosphoric acid, ammonium phosphate, ammonium hydrogen phosphate, ammonium dihydrogen phosphate, phosphorous acid, ammonium hydrogen phosphite, ammonium phosphite; hyprophosphorous acid, ammonium phosphinate, di- and polyacids of phosphorus and their ammonium and ammonium hydrogen salts, pyrophosphates and their ammonium salts, tripolyphosphates and their ammonium salts, metaphosphates and their ammonium salts and mixtures thereof.

In one embodiment, the slurry (a) is formed by mixing said binder with an as-synthesized molecular sieve which has not been fully dried.

In yet a further aspect, the invention resides in a method of making a catalyst composition, the method comprising:

(i) synthesizing a molecular sieve from an aqueous reaction mixture comprising at least one templating agent and at least two of a silicon source, a phosphorus source and an aluminum source; and (ii) recovering the molecular sieve synthesized in (i);

(iii) mixing the molecular sieve recovered in (ii) with a binder or binder precursor and a liquid medium to form a slurry;

(iv) mixing a phosphorus compound with said slurry to produce a phosphorus-containing mixture;

(v) adding a matrix to the phosphorus-containing mixture to produce a catalyst precursor mixture, (vi) spray drying the catalyst precursor mixture to produce particles of said catalyst composition, and then (vii) calcining said catalyst composition particles In one embodiment, the molecular sieve recovered in (ii) is mixed with the binder or binder precursor without being fully dried.

In still a further aspect, the invention resides in a process for converting a feedstock, preferably a feedstock containing an oxygenate, more preferably a feedstock containing an alcohol, and most preferably a feedstock containing methanol, into one or more olefin(s) in the presence of a catalyst composition as described above or as produced by the methods described above.

DETAILED DESCRIPTION OF THE EMBODIMENTS

Introduction

The invention is directed to a catalyst composition comprising a molecular sieve having a framework including at least [AlO$_4$] and [PO$_4$] tetrahedral units, such as an aluminophosphate or a silicoaluminophosphate, to a method of making such a catalyst composition and to the use of such a catalyst composition in the conversion of hydrocarbon feedstocks, particularly oxygenated feedstocks, into olefin(s). It has been found that the addition of a small amount of an external phosphorus compound, typically an inorganic phosphorus compound, during formulation of such a catalyst composition can enhance both the hydrothermal stability and the attrition resistance of the catalyst composition, particularly when used in the conversion of hydrocarbon feedstocks, particularly oxygenated feedstocks, into olefin(s). Moreover, it has been found that these improvements in hydrothermal stability and attrition resistance can be achieved without the dramatic decrease in the surface area of catalyst composition reported in U.S. Pat. No. 6,153,552.

Thus, in one embodiment, in a test involving calcination of the catalyst composition at 760° C. in nitrogen at atmospheric pressure for 3 hours, the present catalyst composition has a microporous surface area in excess of 20%, such as in excess of 50%, conveniently in excess of 75%, and even in excess of 100%, of the microporous surface area of said molecular sieve after calcination at 650° C. in nitrogen at atmospheric pressure for 2 hours.

In another embodiment, after hydrothermal treatment at 800° C. for 18 hours at a water vapor pressure of 45 psig, the catalyst composition retains at least 15% of the methanol conversion activity of the untreated catalyst composition.

In yet another embodiment, the catalyst composition has an attrition rate, as defined by its Attrition Rate Index (ARI), of less than 3 wt % per hour, such as less than 0.95 wt % per hour, for example about 0.05 to about 0.8 wt % per hour.

In addition it has been found that addition of the phosphorus compound can allow a reduction the amount of binder used in formulating the catalyst composition; which is desirable since high binder loadings may result in reduced access to the micropores of the molecular sieve.

The phosphorus compound is introduced into the catalyst composition during formulation by making a slurry of the molecular sieve and a binder or binder precursor, such as aluminum chlorohydrate, in a liquid medium, such as water, and then adding the phosphorus compound to the slurry. After addition of the phosphorus compound, a matrix material, such as a clay, may be added to the slurry and the resultant mixture can then be formed into the desired catalyst particles, such as by spray drying. The resultant catalyst composition can then be calcined.

In one embodiment, phosphorus compound is added to a slurry of a binder or binder precursor and an as-synthesized molecular sieve which has not been fully dried, such as the wet filter cake obtained when an as-synthesized molecular sieve is separated by filtration from the crystallization medium used in synthesizing the sieve.

Molecular Sieve

Molecular sieves have various chemical, physical, and framework characteristics. Molecular sieves have been well classified by the Structure Commission of the International Zeolite Association according to the rules of the IUPAC Commission on Zeolite Nomenclature. A framework-type describes the topology and connectivity of the tetrahedrally coordinated atoms constituting the framework, and makes an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Crystalline molecular sieve materials all have a 3-dimensional, four-connected framework structure of corner-sharing $TO_4$ tetrahedra, where T is any tetrahedrally coordinated cation. Molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B.V., Amsterdam, Netherlands (2001).

Non-limiting examples of molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

The small, medium and large pore molecular sieves have from a 4-ring to a 12-ring or greater framework-type. Typically, the molecular sieves employed herein have 8-, 10- or 12-ring structures and an average pore size in the range of from about 3 Å to 15 Å. More typically, the molecular sieves, preferably silicoaluminophosphate molecular sieves, have 8-rings and an average pore size less than about 5 Å, such as in the range of from 3 Å to about 5 Å, for example from 3 Å to about 4.5 Å, and particularly from 3.5 Å to about 4.2 Å.

Molecular sieves used herein have a molecular framework including at least $[AlO_4]$ and $[PO_4]$ tetrahedral units, such as aluminophosphates (AlPO), and typically including at least $[AlO_4]$ and $[PO_4]$ and $[SiO_4]$ tetrahedral units, such as silicoaluminophosphates (SAPO). These silicon, aluminum, and phosphorus based molecular sieves and metal-containing derivatives thereof have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MaAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in R. Szostak, *Handbook of Molecular Sieves*, Van Nostrand Reinhold, New York, N.Y. (1992), which is herein fully incorporated by reference.

The more preferred molecular sieves are SAPO molecular sieves, and metal-substituted SAPO molecular sieves. Suitable metal substituents are alkali metals of Group IA of the Periodic Table of Elements, an alkaline earth metals of Group IIA of the Periodic Table of Elements, a rare earth metals of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, transition metals of Groups IVB, VB, VIB, VIIB, VIIIB, and IB of the Periodic Table of Elements and mixtures of any of these metal species. In one embodiment, the metal is selected from the group consisting of Co, Cr, Cu, Fe, Ga, Ge, Mg, Mn, Ni, Sn, Ti, Zn and Zr, and mixtures thereof. The metal atoms may be inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements. Preferably M is selected from one of the group consisting of Si, Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Where the molecular sieve is a silicoaluminophosphate or metal-containing silicoaluminophosphate, the SAPO typically has a Si/Al ratio less than 0.65, such as less than 0.40, for example less than 0.32, and particularly less than 0.20. In one embodiment the molecular sieve has a Si/Al ratio in the range of from about 0.65 to about 0.10, such as from about 0.40 to about 0.10, for example from about 0.32 to about 0.10, and particularly from about 0.32 to about 0.15.

Non-limiting examples of SAPO and AlPO molecular sieves useful herein include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, AlPO-5, AlPO-11, AlPO-18, AlPO-31, AlPO-34, AlPO-36, AlPO-37, AlPO-46, and metal containing molecular sieves thereof. Of these, particularly useful molecular sieves are one or a combination of SAPO-18, SAPO-34, SAPO-35, SAPO-44, SAPO-56, AlPO-18 and AlPO-34 and metal containing derivatives thereof, such as one or a combination of SAPO-18, SAPO-34, AlPO-34 and AlPO-18, and metal containing derivatives thereof, and especially one or a combination of SAPO-34 and AlPO-18, and metal containing derivatives thereof.

In an embodiment, the molecular sieve is an intergrowth material having two or more distinct crystalline phases within one molecular sieve composition. In particular, intergrowth molecular sieves are described in U.S. Patent Application Publication No. 2002-0165089 and International Publication No. WO 98/15496 published Apr. 16, 1998, both of which are herein fully incorporated by reference. For example, SAPO-18, AlPO-18 and RUW-18 have an AEI framework-type, and SAPO-34 has a CHA framework-type. Thus the molecular sieve used herein may comprise at least one intergrowth phase of AEI and CHA framework-types, especially where the ratio of CHA framework-type to AEI framework-type, as determined by the DIFFaX method disclosed in U.S. Patent Application Publication No. 2002-0165089, is greater than 1:1.

Molecular Sieve Synthesis

The synthesis of molecular sieves is described in many of the references discussed above. Generally, molecular sieves are synthesized by the hydrothermal crystallization of one or more of a source of aluminum, a source of phosphorus, a source of silicon, water and a templating agent, such as a nitrogen containing organic compound. Typically, a combination of sources of silicon and aluminum or silicon, aluminum and phosphorus, water and optionally one or more templating agents, is placed in a sealed pressure vessel, optionally lined with an inert plastic such as polytetrafluoroethylene, and heated, under a crystallization pressure and temperature, until a crystalline material is formed, which can then recovered by filtration, centrifugation and/or decanting.

Non-limiting examples of silicon sources include silicates, fumed silica, for example, Aerosil-200 available from Degussa Inc., New York, N.Y., and CAB-O-SIL M-5, organosilicon compounds such as tetraalkylorthosilicates, for example, tetramethylorthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid or any combination thereof.

Non-limiting examples of aluminum sources include aluminum alkoxides, for example aluminum isopropoxide, aluminum phosphate, aluminum hydroxide, sodium aluminate, pseudo-boehmite, gibbsite and aluminum trichloride, or any combination thereof. A convenient source of aluminum is pseudo-boehmite, particularly when producing a silicoaluminophosphate molecular sieve.

Non-limiting examples of phosphorus sources, which may also include aluminum-containing phosphorus compositions, include phosphoric acid, organic phosphates such as triethyl phosphate, and crystalline or amorphous aluminophosphates such as $AlPO_4$, phosphorus salts, or combinations thereof. A convenient source of phosphorus is phosphoric acid, particularly when producing a silicoaluminophosphate.

Templating agents are generally compounds that contain elements of Group 15 of the Periodic Table of Elements, particularly nitrogen, phosphorus, arsenic and antimony. Typical templating agents also contain at least one alkyl or aryl group, such as an alkyl or aryl group having from 1 to 10 carbon atoms, for example from 1 to 8 carbon atoms. Preferred templating agents are often nitrogen-containing compounds, such as amines, quaternary ammonium compounds and combinations thereof. Suitable quaternary ammonium compounds are represented by the general formula $R_4N^+$, where each R is hydrogen or a hydrocarbyl or substituted hydrocarbyl group, preferably an alkyl group or an aryl group having from 1 to 10 carbon atoms.

Non-limiting examples of templating agents include tetraalkyl ammonium compounds including salts thereof, such as tetramethyl ammonium compounds, tetraethyl ammonium compounds, tetrapropyl ammonium compounds, and tetrabutylammonium compounds, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butyl-amine, ethylenediamine, pyrrolidine, and 2-imidazolidone.

The pH of the synthesis mixture containing at a minimum a silicon-, aluminum-, and/or phosphorus-composition, and a templating agent, is generally in the range of from 2 to 10, such as from 4 to 9, for example from 5 to 8.

Generally, the synthesis mixture described above is sealed in a vessel and heated, preferably under autogenous pressure, to a temperature in the range of from about 80° C. to about 250° C., such as from about 100° C. to about 250° C., for example from about 125° C. to about 225° C., such as from about 150° C. to about 180° C.

In one embodiment, the synthesis of a molecular sieve is aided by seeds from another or the same framework type molecular sieve.

The time required to form the crystalline product is usually dependent on the temperature and can vary from immediately up to several weeks. Typically the crystallization time is from about 30 minutes to around 2 weeks, such as from about 45 minutes to about 240 hours, for example from about 1 hour to about 120 hours. The hydrothermal crystallization may be carried out with or without agitation or stirring.

One method for crystallization involves subjecting an aqueous reaction mixture containing an excess amount of a templating agent, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Other methods for synthesizing molecular sieves or modifying molecular sieves are described in U.S. Pat. No. 5,879,655 (controlling the ratio of the templating agent to phosphorus), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorus modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

Once the crystalline molecular sieve product is formed, usually in a slurry state, it may be recovered by any standard technique well known in the art, for example, by centrifugation or filtration. The recovered crystalline product, normally termed the "wet filter cake", may then be washed, such as with water, and then dried, such as in air, before being formulated into a catalyst composition. Alternatively, as will be discussed in more detail below, in the present catalyst formulation method, the wet filter cake may be formulated into a catalyst composition directly, that is without any drying, or after only partial drying.

Where a templating agent is used in the synthesis of the molecular sieve, any templating agent retained in the product may be removed after crystallization by numerous well known techniques, for example, by calcination. Calcination involves contacting the molecular sieve containing the templating agent with a gas, preferably containing oxygen, at any desired concentration at an elevated temperature sufficient to either partially or completely remove the templating agent.

Phosphorus Compound

The catalyst composition employed herein contains a phosphorus compound separate from any phosphorus contained by said molecular sieve. The phosphorus source may be an organic phosphorus compound, but is preferably an inorganic phosphorus compound and more preferably is soluble in water. Suitable phosphorus compounds include acids and their derivative salts such as (1) higher ($P^{5+}$ and $P^{3+}$) acids and salts, for example phosphoric acid ($H_3PO_4$), ammonium phosphate, ammonium hydrogen phosphate, ammonium dihydrogen phosphate and phosphorus acid ($H_3PO_3$), which is bifunctional, forming salts such as ammonium hydrogen phosphite and ammonium phosphite; (2) lower acids and salts, for example, hyprophosphorous acid ($H_3PO_2$) and ammonium phosphinate; (3) di- and polyacids and salts, for example, $H_4P_2O_4$, $H_4P_2O_5$, $H_4P_2O_6$, $H_5P_3O_8$ and their ammonium and ammonium hydrogen salts; (4) condensed phosphates, for example, pyrophosphates ($M^1_4P_2O_7$), tripolyphosphates ($M^I_4P_3O_{10}$) and metaphosphates ($M^1_3P_3O_9$ and $M^1_4P_4O_2$). Description of the preparation and properties of these phosphorus compounds can be found in "Advanced Inorganic Chemistry", by F. A. Cotton, G. Wilkinson, 5th Edition, pp. 421–427, John Wiley & Sons, New York, 1988, the entire disclosure of which is fully incorporated herein by reference.

Other phosphorus salts can also be used as long as the cations introduced do not interfere the oxygenate to olefin reaction of the molecular sieve, for instance, use of alkali and alkaline salts in high levels will lead to reduction of number of acid sites of the catalyst unless these cations introduced are removed using addition ion exchange steps, e.g., ion exchange with ammonium salt solution or acid solution.

As will discussed in more detail below, the phosphorus compound is added during formulation of the catalyst composition and, in particular, to a slurry of the molecular sieve and a binder or binder precursor.

The amount of phosphorus compound added during formulation of the catalyst composition is typically such that the final catalyst composition contains between about 0.05 and about 15 wt %, for example between about 0.1 and about 10 wt %, such as between about 0.5 and about 6 wt %, and conveniently between greater 1.0 and about 5 wt %, of phosphorus expressed as $P_2O_5$, by weight of the catalyst composition.

Binder and/or Matrix Material

In producing a catalyst composition, the molecular sieve and phosphorus compound described above are combined with a binder or binder precursor and typically also with a matrix material. The resulting combination can then be formed into particles of the desired size and shape by well-known techniques such as spray drying, pelletizing, extrusion, and the like.

There are many different binders that are useful in forming catalyst compositions. Non-limiting examples of binders that are useful alone or in combination include various types of hydrated alumina, silicas, and/or other inorganic oxide sols. One preferred alumina containing sol is aluminum chlorohydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide binder component. For example, an alumina sol will convert to an aluminum oxide binder following heat treatment.

Aluminum chlorohydrate, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binder is an alumina sol, predominantly comprising aluminum oxide, optionally including some silicon. In yet another embodiment, the binder is peptized alumina made by treating an alumina hydrate, such as pseudobohemite, with an acid, preferably an acid that does not contain a halogen, to prepare a sol or aluminum ion solution. Non-limiting examples of commercially available colloidal alumina sols include Nalco 8676 available from Nalco Chemical Co., Naperville, Ill., and Nyacol AL20DW available from Nyacol Nano Technologies, Inc., Ashland, Mass.

In one embodiment, the weight ratio of the binder to the molecular sieve is in the range of from about 0.1 to 0.5, such as in the range of from 0.1 to less than 0.5, for example in the range of from 0.11 to 0.48, conveniently from 0.12 to about 0.45, typically from 0.13 to less than 0.45, and particularly in the range of from 0.15 to about 0.4. In another embodiment, the weight ratio of the binder to the molecular sieve is in the range of from 0.11 to 0.45, such as in the range of from about 0.12 to less than 0.40, for example in the range of from 0.15 to about 0.35, and conveniently in the range of from 0.2 to about 0.3.

Where the catalyst composition contains a matrix material, this is preferably different from the active metal oxide and any binder. Matrix materials are typically effective in reducing overall catalyst cost, acting as thermal sinks to assist in shielding heat from the catalyst composition for example during regeneration, densifying the catalyst composition, and increasing catalyst strength such as crush strength and attrition resistance.

Non-limiting examples of matrix materials include one or more of rare earth metal oxides, non-active metal oxides including magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. The matrix material, such as a clay, may be subjected to well known modification processes such as calcination and/or acid treatment and/or chemical treatment.

In a preferred embodiment, the matrix material is a clay or a clay-type composition, particularly having a low iron or titania content, and most preferably is kaolin. Kaolin has been found to form a pumpable, high solids content slurry, to have a low fresh surface area, and to pack together easily due to its platelet structure. A preferred average particle size of the matrix material, most preferably kaolin, is from about 0.1 µm to about 0.6 µm with a $D_{90}$ particle size distribution of less than about 1 µm.

Where the catalyst composition contains a binder and a matrix material, the weight ratio of the binder to the matrix material is typically from 1:15 to 1:5, such as from 1:10 to 1:4, and particularly from 1:6 to 1:5. The amount of binder is typically from about 2% by weight to about 30% by weight, such as from about 5% by weight to about 20% by weight, and particularly from about 7% by weight to about 15% by weight, based on the total weight of the binder, the molecular sieve and matrix material. It has been found that a higher sieve content and lower matrix content increases the molecular sieve catalyst composition performance, whereas a lower sieve content and higher matrix content improves the attrition resistance of the composition.

In general, the amount of binder and/or matrix material is such that the formulated molecular sieve catalyst composition contains from about 1% to about 99%, such as from about 10% to about 90%, such as about 10% to about 80%, for example from about 20% to about 70%, and conveniently from about 25% to about 60% by weight of the molecular sieve based on the total weight of the molecular sieve catalyst composition.

Method of Making the Catalyst Composition

In making the catalyst composition of the invention, a molecular sieve as described above is formed into a slurry with a binder or binder precursor and a liquid medium, such as water, and then the phosphorus compound is added to the slurry. After addition of the phosphorus compound, a matrix material may be added to the slurry and the resultant mixture can then be formed into the desired catalyst particles, such as by spray drying. The resultant catalyst composition can then be calcined.

In one embodiment, the molecular sieve used to form the slurry with the binder or binder precursor is in its as-synthesized state and has not been fully dried. As used herein, the term "not fully dried" is defined to include no drying up to not calcining the crystalline molecular sieve material. In addition, the term "partially dried" is used herein to include drying the crystalline molecular sieve material to a level wherein after drying the amount of templating agent associated with the molecular sieve is in the range of from about 50, such as from about 60, for example from about 70, and preferably from about 80 weight percent to 100 weight percent of the original amount of templating agent used to form the molecular sieve originally.

For example, the molecular sieve used to form the slurry with the binder or binder precursor can be the wet filter cake resulting from separation of the as-synthesized molecular sieve from the liquid, normally aqueous, crystallization medium. The wet filter cake can be used directly, without any intermediate washing and/or dehydration.

Alternatively, the as-synthesized molecular sieve, without or without previous washing, can be dried, preferably in air, to a level such that the amount of liquid medium, usually water, contained by the molecular sieve is in the range of from about 0 weight percent to about 80 weight percent liquid, such as in the range of from greater than 5 weight percent to about 70 weight percent, for example from about 10 weight percent to about 70 weight percent, and conveniently from about 20 weight percent to about 60 weight percent based on the total weight of the synthesized molecular sieve and liquid.

Determination of the percentage of liquid medium and the percentage of template for purposes of this specification uses a Thermal Gravimetric Analysis (TGA) technique as follows. An amount the molecular sieve material, the sample, is loaded into a sample pan of a Cahn TG-121 Microbalance, available from Cahn Instrument, Inc., Cerritos, Calif. During the TGA technique, a flow of 114 cc/min (STP) air is used. The sample is then heated from 25° C. to 180° C. at 30° C./min and held at 180° C. for 3 hours or until the weight of the sample becomes constant. The weight loss of the sample expressed as a percentage of the original sample weight is then treated as the percentage of the liquid medium. Subsequently, the sample is heated at 30° C./min from 180° C. to 650° C. and held at 650° C. for 2 hours. The additional weight loss expressed as a percentage of the original sample weight is regarded as the weight loss of the templating agent. The total weight loss during the entire TGA treatment expressed as a percentage of the original sample weight is defined as Loss-On-Ignition (LOI).

In formulating the catalyst composition, the binder or binder precursor and the molecular sieve are initially combined in the presence of a liquid to form a slurry typically containing in the range of from about 25 weight percent to about 55 weight percent, such as from about 30 weight percent to 50 weight percent, solid particles, of which from about 20 weight percent to about 90 weight percent, such as from about 25 weight percent to about 85 weight percent, comprise the molecular sieve. The liquid used to form the slurry can, for example, be one or a combination of water, an alcohol, a ketone, an aldehyde, and/or an ester, but normally will be water.

The slurry is milled to form a substantially homogeneous mixture and then a phosphorus compound as described above, either in solid form or as a liquid solution, is added to the slurry. The resultant mixture is further milled to ensure even dispersion of the phosphorus compound and then a matrix material is added to the mixture, typically such that the matrix-containing mixture contains in the range of from about 25 weight percent to about 55 weight percent, such as from about 30 weight percent to 50 weight percent, solid particles.

The matrix-containing mixture is milled to form a substantially homogeneous catalyst precursor mixture having the desired particle size distribution, for example such that at least 90 percent of the solid particles having a diameter less than 20 μm, preferably less than 10 μm. Typically the catalyst precursor mixture contains in the range of from about 25 weight percent to about 55 weight percent, such as from about 30 weight percent to 50 weight percent, solid particles. In addition, the catalyst precursor mixture contains from about 20 to about 90 weight percent, such as from about 25 to about 85 weight percent, of the molecular sieve, from about 2 to about 25 weight percent, such as from about 3 to about 23 weight percent, of the binder or binder precursor, from about 5 to about 85 weight percent, such as from about 10 to about 80 weight percent, of the matrix material, and from about 0.05 to about 15 weight percent, such as from about 0.1 to about 10 weight percent, of the phosphorus compound.

The catalyst precursor mixture is then fed to a forming unit that produces the molecular sieve catalyst composition. In a preferred embodiment, the forming unit is spray dryer. Typically, the forming unit is maintained at a temperature sufficient to remove most of the liquid from the precursor mixture, and from the resulting molecular sieve catalyst composition. The resulting catalyst composition when formed in this way takes the form of microspheres.

When a spray drier is used as the forming unit, typically, the precursor mixture is fed to the spray drying volume with a drying gas with an average inlet temperature ranging from 100° C. to 550° C., and a combined outlet temperature ranging from 50° C. to about 225° C. In an embodiment, the average diameter of the spray dried formed catalyst composition is from about 30 μm to about 300 μm, such as from about 40 μm to about 250 μm, for example from about 50 μm to about 200 μm, and conveniently from about 55 μm to about 100 μm.

For example, the catalyst precursor mixture may be directed onto the perimeter of a spinning wheel that distributes the mixture into small droplets, the size of which is controlled by many factors including mixture viscosity, surface tension, flow rate, pressure, the temperature of the slurry, the shape and dimension of the nozzle(s), and the spinning rate of the wheel. These droplets are then dried in a co-current or counter-current flow of air passing through a spray drier to form a substantially dried or dried molecular sieve catalyst composition, more specifically a molecular sieve composition in a powder or a microsphere form.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

Once the molecular sieve catalyst composition is formed in a substantially dry or dried state, to further harden and/or activate the formed catalyst composition, a heat treatment such as calcination, at an elevated temperature is usually performed. Typical calcination temperatures are in the range from about 400° C. to about 1,000° C., such as from about 500° C. to about 850° C., such as from about 600° C. to about 800° C. The calcination environment is not critical and typically can include air (which may contain a small amount of water vapor), nitrogen, helium, flue gas (combustion product lean in oxygen), or any combination thereof. For example, although calcination in nitrogen may be employed in various tests used in the present specification, it should be understood that calcination in nitrogen is not essential in producing the catalyst composition of the invention.

In one practical embodiment, the catalyst composition is heated in nitrogen at a temperature of from about 700° C. to about 800° C. Heating is carried out for a period of time typically from 30 minutes to 15 hours, such as from 1 hour to about 10 hours, for example from about 1 hour to about 5 hours, and particularly from about 2 hours to about 4 hours.

The resultant molecular sieve catalyst composition typically has a micropore surface area (MSA) in the range of from about 400 $m^2$/g-molecular sieve to about 600 $m^2$/g-molecular sieve, for example in the range of from 425 $m^2$/g-molecular sieve to about 550 $m^2$/g-molecular sieve, and conveniently in the range of from about 450 $m^2$/g-molecular sieve to about 550 $m^2$/g-molecular sieve. Moreover, the catalyst composition exhibits a high degree of thermal stability such that in a test involving calcination in nitrogen at 760° C. and atmospheric pressure for 3 hours, the catalyst composition has an MSA in excess of 20%, such as in excess of 50%, conveniently in excess of 75%, and even in excess of 100%, of the MSA of said molecular sieve after calcination at 650° C. in nitrogen at atmospheric pressure for 2 hours.

The catalyst composition also exhibits improved hydrothermal stability as evidenced by, for example, the retention of its activity for converting methanol to olefins after high temperature hydrothermal treatment such as would be experienced during regeneration. Thus in one embodiment, after hydrothermal treatment at 800° C. for 18 hours at a water vapor pressure of 45 psig, the present catalyst composition retains at least 15%, such as at least 20%, and generally at least 25% of the methanol conversion activity of the untreated catalyst composition.

In addition, the molecular sieve catalyst composition has improved attrition resistance as determined by its Attrition Rate Index (ARI), which measures the weight percent catalyst composition attrited per hour in a standardized attrition test. In particular, ARI is measured by adding 6.0 g of catalyst composition having a particle size ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour and the fines collected in the thimble are removed from the unit. A new thimble is then installed and the catalyst left in the attrition unit is attrited for an additional 3 hours, under the same gas flow and moisture levels. The fines collected in the thimble are recovered. The collection of fine catalyst particles separated by the thimble after the first hour are weighed.

The amount in grams of fine particles divided by the original amount of catalyst charged to the attrition cup expressed on per hour basis is the ARI, in weight percent per hour. ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

Typically, the molecular sieve catalyst composition has an ARI less than 5 weight percent per hour, such as less than 3 weight percent per hour, such as less than 1 weight percent per hour, and for example less than 0.95 weight percent per hour. In one embodiment, the molecular sieve catalyst composition has an ARI in the range of from 0.05 weight percent per hour to less than 3 weight percent per hour, such as from about 0.05 weight percent per hour to less than 0.95 weight percent per hour, and for example from about 0.05 weight percent per hour to 0.8 weight percent per hour.

In one practical embodiment of the invention, the molecular sieve catalyst composition comprises a molecular sieve in an amount of from 25 weight percent to 85 weight percent, a phosphorus compound in an amount of from 0.5 to 6 weight percent expressed as $P_2O_5$, a binder in an amount of from 3 to 23 weight percent, and a matrix material in an amount of from 5 to 85 weight percent, based on the total weight of the catalyst composition, after calcination, has an MSA from 450 $m^2$/g-molecular sieve to 550 $m^2$/g-molecular sieve, and an ARI less than 0.95 weight percent per hour.

Process for Using the Molecular Sieve Catalyst Compositions

The catalyst compositions described above are useful in a variety of processes including cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene; polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecyclization; disproportionation, of for example toluene to make benzene and paraxylene; oligomerization, of for example straight and branched chain olefin(s); and dehydrocyclization.

Preferred processes include processes for converting naphtha to highly aromatic mixtures; converting light olefin(s) to gasoline, distillates and lubricants; converting oxygenates to olefin(s); converting light paraffins to olefins and/or aromatics; and converting unsaturated hydrocarbons (ethylene and/or acetylene) to aldehydes for conversion into alcohols, acids and esters.

The most preferred process of the invention is a process directed to the conversion of a feedstock to one or more olefin(s). Typically, the feedstock contains one or more aliphatic-containing compounds such that the aliphatic moiety contains from 1 to about 50 carbon atoms, such as from 1 to 20 carbon atoms, for example from 1 to 10 carbon atoms, and particularly from 1 to 4 carbon atoms.

Non-limiting examples of aliphatic-containing compounds include alcohols such as methanol and ethanol, alkyl mercaptans such as methyl mercaptan and ethyl mercaptan, alkyl sulfides such as methyl sulfide, alkylamines such as methylamine, alkyl ethers such as dimethyl ether, diethyl ether and methylethyl ether, alkyl halides such as methyl chloride and ethyl chloride, alkyl ketones such as dimethyl ketone, formaldehydes, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) produced from the feedstock typically have from 2 to 30 carbon atoms, preferably 2 to 8 carbon atoms, more preferably 2 to 6 carbon atoms, still more preferably 2 to 4 carbons atoms, and most preferably are ethylene and/or propylene.

The catalyst composition of the invention is particularly useful in the process that is generally referred to as the gas-to-olefins (GTO) process or alternatively, the methanol-to-olefins (MTO) process. In this process, an oxygenated feedstock, most preferably a methanol-containing feedstock, is converted in the presence of a molecular sieve catalyst composition into one or more olefin(s), preferably and predominantly, ethylene and/or propylene.

Using the catalyst composition of the invention for the conversion of a feedstock, preferably a feedstock containing one or more oxygenates, the amount of olefin(s) produced based on the total weight of hydrocarbon produced is greater than 50 weight percent, typically greater than 60 weight percent, such as greater than 70 weight percent, and preferably greater than 75 weight percent. In one embodiment, the amount of ethylene and/or propylene produced based on the total weight of hydrocarbon product produced is greater than 65 weight percent, such as greater than 70 weight percent, for example greater than 75 weight percent, and preferably greater than 78 weight percent. Typically, the amount ethylene produced in weight percent based on the total weight of hydrocarbon product produced, is greater than 30 weight percent, such as greater than 35 weight percent, for example greater than 40 weight percent. In addition, the amount of propylene produced in weight percent based on the total weight of hydrocarbon product produced is greater than 20 weight percent, such as greater than 25 weight percent, for example greater than 30 weight percent, and preferably greater than 35 weight percent.

In addition to the oxygenate component, such as methanol, the feedstock may contains one or more diluent(s), which are generally non-reactive to the feedstock or molecular sieve catalyst composition and are typically used to reduce the concentration of the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, for example water, may be used either in a liquid or a vapor form, or a combination thereof. The diluent may be either added directly to the feedstock entering a reactor or added directly to the reactor, or added with the molecular sieve catalyst composition.

The present process can be conducted over a wide range of temperatures, such as in the range of from about 200° C. to about 1000° C., for example from about 250° C. to about 800° C., including from about 250° C. to about 750 ° C., conveniently from about 300° C. to about 650° C., typically from about 350° C. to about 600° C. and particularly from about 350° C. to about 550° C.

Similarly, the present process can be conducted over a wide range of pressures including autogenous pressure. Typically the partial pressure of the feedstock exclusive of any diluent therein employed in the process is in the range of from about 0.1 kPaa to about 5 MPaa, such as from about 5 kPaa to about 1 MPaa, and conveniently from about 20 kPaa to about 500 kPaa.

The weight hourly space velocity (WHSV), defined as the total weight of feedstock excluding any diluents per hour per weight of molecular sieve in the catalyst composition, typically ranges from about 1 $hr^{-1}$ to about 5000 $hr^{-1}$, such as from about 2 $hr^{-1}$ to about 3000 $hr^{-1}$, for example from about 5 $hr^{-1}$ to about 1500 $hr^{-1}$, and conveniently from about 10 $hr^{-1}$ to about 1000 $hr^{-1}$. In one embodiment, the WHSV is greater than 20 $hr^{-1}$ and, where feedstock contains methanol and/or dimethyl ether, is in the range of from about 20 $hr^{-1}$ to about 300 $hr^{-1}$.

Where the process is conducted in a fluidized bed, the superficial gas velocity (SGV) of the feedstock including diluent and reaction products within the reactor system, and particularly within a riser reactor(s), is at least 0.1 meter per second (m/sec), such as greater than 0.5 m/sec, such as greater than 1 m/sec, for example greater than 2 m/sec, conveniently greater than 3 m/sec, and typically greater than 4 m/sec. See for example U.S. patent application Ser. No. 09/708,753 filed Nov. 8, 2000, which is herein incorporated by reference.

The process of the invention is conveniently conducted as a fixed bed process, or more typically as a fluidized bed process (including a turbulent bed process), such as a continuous fluidized bed process, and particularly a continuous high velocity fluidized bed process.

The process can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In one practical embodiment, the process is conducted as a fluidized bed process or high velocity fluidized bed process utilizing a reactor system, a regeneration system and a recovery system.

In such a process the reactor system conveniently includes a fluid bed reactor system having a first reaction zone within one or more riser reactor(s) and a second reaction zone within at least one disengaging vessel, typically comprising one or more cyclones. In one embodiment, the one or more riser reactor(s) and disengaging vessel are contained within a single reactor vessel. Fresh feedstock, preferably containing one or more oxygenates, optionally with one or more diluent(s), is fed to the one or more riser reactor(s) into which a molecular sieve catalyst composition or coked version thereof is introduced. In one embodiment, prior to being introduced to the riser reactor(s), the molecular sieve catalyst composition or coked version thereof is contacted with a liquid, preferably water or methanol, and/or a gas, for example, an inert gas such as nitrogen.

In an embodiment, the amount of fresh feedstock fed as a liquid and/or a vapor to the reactor system is in the range of from 0.1 weight percent to about 85 weight percent, such as from about 1 weight percent to about 75 weight percent, more typically from about 5 weight percent to about 65 weight percent based on the total weight of the feedstock including any diluent contained therein. The liquid and vapor feedstocks may be the same composition, or may contain varying proportions of the same or different feedstocks with the same or different diluents.

The feedstock entering the reactor system is preferably converted, partially or fully, in the first reactor zone into a gaseous effluent that enters the disengaging vessel along with the coked catalyst composition. In the preferred embodiment, cyclone(s) are provided within the disengaging vessel to separate the coked catalyst composition from the gaseous effluent containing one or more olefin(s) within the disengaging vessel. Although cyclones are preferred, gravity effects within the disengaging vessel can also be used to separate the catalyst composition from the gaseous effluent. Other methods for separating the catalyst composition from the gaseous effluent include the use of plates, caps, elbows, and the like.

In one embodiment, the disengaging vessel includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition that is then introduced to the regeneration system.

The coked catalyst composition is withdrawn from the disengaging vessel and introduced to the regeneration system. The regeneration system comprises a regenerator where the coked catalyst composition is contacted with a regeneration medium, preferably a gas containing oxygen, under conventional regeneration conditions of temperature, pressure and residence time.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example from about 450° C. to about 750° C., and conveniently from about 550° C. to about 700° C. The regeneration pressure may be in the range of from about 15 psia (103 kPaa) to about 500 psia (3448 kPaa), such as from about 20 psia (138 kPaa) to about 250 psia (1724 kPaa), including from about 25 psia (172 kPaa) to about 150 psia (1034 kPaa), and conveniently from about 30 psia (207 kPaa) to about 60 psia (414 kPaa).

The residence time of the catalyst composition in the regenerator may be in the range of from about one minute to several hours, such as from about one minute to 100 minutes, and the volume of oxygen in the regeneration gas may be in the range of from about 0.01 mole percent to about 5 mole percent based on the total volume of the gas.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916 (controlling moisture), which is herein fully incorporated by reference.

The regenerated catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In one embodiment, the regenerated catalyst composition withdrawn from the regeneration system is returned to the riser reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more riser reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, *Experimental Techniques, Circulating Fluidized Beds*, Grace, Avidan and Knowlton, eds., Blackie, 1997 (336–337), which is herein incorporated by reference.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from about 0.1 weight percent to about 10 weight percent, for example from about 0.2 weight percent to about 5 weight percent, and conveniently from about 0.3 weight percent to about 2 weight percent based on the weight of the molecular sieve.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment, for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a dethanizer, a depropanizer, a wash tower often referred to as a caustic wash tower and/or quench tower, absorbers, adsorbers, membranes, ethylene (C2) splitter, propylene (C3) splitter and butene (C4) splitter.

Various recovery systems useful for recovering olefin(s), such as ethylene, propylene and/or butene, are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which are herein incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Typically, in converting one or more oxygenates to olefin(s) having 2 or 3 carbon atoms, a minor amount hydrocarbons, particularly olefin(s), having 4 or more carbon atoms is also produced. The amount of $C_4+$ hydrocarbons is normally less than 20 weight percent, such as less than 10 weight percent, for example less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products.

Non-limiting examples of such reaction systems are described in U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading C3, C4 and C5 Olefinic Streams*, Pet. & Coal, Vol. 37, No. 4 (1995) (dimerizing or oligomerizing propylene, butylene and pentylene), which are all fully herein incorporated by reference.

The preferred light olefin(s) produced by any one of the processes described above are high purity prime olefin(s) products that contain a single carbon number olefin in an amount greater than 80 percent, such as greater than 90 weight percent, such as greater than 95 weight percent, for example at least about 99 weight percent, based on the total weight of the olefin.

In one practical embodiment, the process of the invention forms part of an integrated process for producing light olefin(s) from a hydrocarbon feedstock, preferably a gaseous hydrocarbon feedstock, particularly methane and/or ethane. The first step in the process is passing the gaseous feedstock, preferably in combination with a water stream, to a syngas production zone to produce a synthesis gas (syngas) stream, typically comprising carbon dioxide, carbon monoxide and hydrogen. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material. Preferably synthesis gas stream is produced via steam reforming of natural gas.

The next step in the process involves contacting the synthesis gas stream generally with a heterogeneous catalyst, typically a copper based catalyst, to produce an oxygenate containing stream, often in combination with water. In one embodiment, the contacting step is conducted at temperature in the range of from about 150° C. to about 450° C. and a pressure in the range of from about 5 MPa to about 10 MPa.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fuel oil. The oxygenate containing stream, crude methanol, in the preferred embodiment is passed through a well known purification processes, distillation, separation and fractionation, resulting in a purified oxygenate containing stream, for example, commercial Grade A and AA methanol.

The oxygenate containing stream or purified oxygenate containing stream, optionally with one or more diluents, can then be used as a feedstock in a process to produce light olefin(s), such as ethylene and/or propylene. Non-limiting examples of this integrated process are described in EP-B-0 933 345, which is herein fully incorporated by reference.

In another more fully integrated process, that optionally is combined with the integrated processes described above, the olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above. However, the preferred polymerization catalysts are the Ziegler-Natta, Phillips-type, metallocene, metallocene-type and advanced polymerization catalysts, and mixtures thereof.

In a preferred embodiment, the integrated process comprises a process for polymerizing one or more olefin(s) in the presence of a polymerization catalyst system in a polymerization reactor to produce one or more polymer products, wherein the one or more olefin(s) have been made by converting an alcohol, particularly methanol, using a molecular sieve catalyst composition as described above. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

EXAMPLES

In order to provide a better understanding of the present invention including representative advantages thereof, the following examples are offered.

Constituents of a mixture used for formulating catalysts will generally contain volatile components, including, but not limited to, water and, in the case of molecular sieve, organic template. It is common practice to describe the amount or proportion of these constituents as being on a "calcined basis". On a "calcined basis" is defined herein as the amount or fraction of each component remaining after it has been mathematically reduced to account for losses in weight expected to occur if the component had been calcined. Thus, 10 grams of a component containing 25% template would be described as "7.5 g on a calcined basis".

Synthesis of a SAPO-34 molecular sieve is well known, and in the Examples below has a MSA of about 450 m²/g to 550 m²/g-molecular sieve. Micropore surface area (MSA) is a measurement of the amount of micropores present in a porous material. MSA is the difference between the total surface area (BET surface area), determined from relative pressures that give a linear plot, and the external surface area, calculated from the slope of the linear region of the t-plot with a small correction to put it on the same basis as the BET surface area. This approach has been used for determining the amount of zeolite in cracking catalysts by Johnson [M. F. L. Johnson, J. Catal., 52, 425–431 (1978)]. The t-plot is a transformation of the adsorption isotherm in which relative pressure is replaced by t, the statistical thickness of the adsorbed layer on nonporous material at the corresponding relative pressure; see Lippens and de Boer for determining various characteristics of pore systems, such as pore shapes [B. C. Lippens, and J. H. de Boer, J. Catal., 4, 319 (1965)]. Sing [K. S. W. Sing, Chem. Ind., 829 (1967)] has introduced that the extrapolation of a linear t-plot to t=0 can yield the volume of micropores.

MSA is determined using a MICROMERITICS Gemini 2375 from Micromeritics Instrument Corporation, Norcross, Ga. The procedure involves loading an amount, 0.15 g to 0.6 g, of a sample into the sample cell for degassing at 300° C. for a minimum of 2 hours. During the analysis, the Evacuation Time is 1.0 minute, no free space is used, and the sample density is 1.0 g/cc. Thirteen (13) adsorption data points are collected with adsorption targets of:

| Data Point | Adsorption Target (p/p$_0$) | Data Point | Adsorption Target (p/p$_0$) |
|---|---|---|---|
| 1 | 0.00500 | 8 | 0.25000 |
| 2 | 0.07500 | 9 | 0.30000 |
| 3 | 0.01000 | 10 | 0.40000 |
| 4 | 0.05000 | 11 | 0.60000 |
| 5 | 0.10000 | 12 | 0.75000 |
| 6 | 0.15000 | 13 | 0.95000 |
| 7 | 0.20000 | | |

The correction factor used in the t-plot is 0.975. No de-sorption points are collected. Other analysis parameters include, Analysis Mode: Equilibrate; Equilibration Time: 5 second; Scan Rate: 10 seconds. A t-plot from 0.00000 to 0.90000 is constructed using the ASTM certified form of the Harkins and Jura equation (H-J Model): $t(p)=(13.99/(0.034-\log(p/p_o)))^{0.5}$. It is shown by Cape and Kibby [J. A. Cape and C. L. Kibby, J. Colloids and Interface Science, 138, 516–520 (1990)] that the conventional BET surface area of a microporous material can be decomposed quantitatively into the external area and the micropore volume, as expressed by equation given below: $S_{micro}=S_{tot}-S_{ext}=v_m/d_j$, where $v_m$ is the micropore volume, $S_{micro}$ is the micropore area calculated from $S_{tot}$ and $S_{ext}$. $S_{tot}$ is given by the conventional BET method, and $S_{ext}$ is the external area taken from the t-plot. The proportionality factor, $d_j$ is a nonphysical length the value of which depends on the pressure used in the experiments and is determined quantitatively by the pressures used in the BET fits.

Viscosity measurements were conducted using a Brookfield DV-E viscometer from Brookfield Engineering Laboratories Inc., Middleboro, Mass. and using a #3 spindle at various spindle rotation speeds ranging from 10 RPM to 100 RPM. The measurements were made on slurry sample at room temperature.

Example 1 (Comparative)

A catalyst precursor slurry containing 45 wt % solids (on a calcined basis) and composed of 40 wt % SAPO-34 molecular sieve that had not been completely dried or calcined, 10.6 wt % Al$_2$O$_3$ binder, and 49.4 wt % clay matrix material was prepared according to the following procedure.

A SAPO-34 molecular sieve wet filter cake was recovered from a conventional hydrothermal synthesis process and 1703.84 g of deionized water was added to 2988.93 g of the wet filter cake (1621.29 g on a calcined basis). The resultant slurry was mixed at 1500 RPM using a Yamato 4000D mixer (Yamato Scientific America Inc., Orangeburg, N.Y.) for 15 minutes, and then subjected to a high-shear treatment using a Silverson L4RT-A high shear mixer at 6000 RPM for 10 minutes. The resultant slurry had a pH value of 6.3 measured at 26° C.

869.03 g (429.64 g on a calcined basis) of Reheis Micro-Dry aluminum chlorohydrate (Reheis Inc., Berkeley Heights, N.J.) was added to 859.12 g of deionized water and mixed at 1500 RPM using a Yamato 4000D mixer for 15 minutes followed by a high-shear treatment using the Silverson high shear mixer at 6000 RPM for 10 minutes. This solution had a pH of 3.3 measured at 31° C.

The SAPO-34 molecular sieve slurry and aluminum chlorohydrate solution were combined and mixed at 1500 RPM using the Yamato 4000D mixer for 15 minutes, and then mixed using the Silverson high-shear mixer at 6000 RPM for 10 minutes. The resultant slurry had a pH value of 4.2 measured at 30° C.

2302.3 g (2002.30 g on a calcined basis) of Engelhard ASP Ultrafine kaolin clay (Engelhard Corporation, Iselin, N.J.) was added to the SAPO-34/aluminum chlorohydrate slurry under constant mixing at 250 to 400 RPM, and then mixed at 1500 RPM using a Yamato 4000D mixer for 15 minutes followed by high-shear mixing using the Silverson mixer at 6000 RPM for 10 minutes. The solids content of the slurry was then adjusted to 45 wt % solids by the addition of 283.97 g of deionized water followed by mixing at 1500 RPM for 15 minutes using the Yamato mixer and then high-shear mixing using the Silverson mixer at 6000 RPM for 10 minutes. The final catalyst precursor slurry had a pH value of 3.8 measured at 36° C. and a weight ratio of binder to molecular sieve of about 0.265. The viscosity of the slurry at 10 rpm was 4920 cps.

750 g of the catalyst precursor slurry was then spray dried using a Yamato DL-41 spray dryer (Yamato Scientific America, Orangeburg, N.Y.) operated in a down spray mode using an atomization nozzle of 1 mm. The spray drying conditions included a feed rate of 40 g/min, an inlet temperature of 350° C., an atomization pressure of 14 psig (96.5 kPag) and a carrier gas (nitrogen) flow at 60% of full setting. The spray dried catalyst product was collected in a cyclone and was then calcined in a muffle furnace at 650° C. in air for 2 hours. The calcined catalyst composition had an ARI of 0.95 weight percent per hour, an MSA of 489.5 m$^2$/g of molecular sieve and an apparent bulk density of 0.78 g/cc. After calcination at 760° C. for 3 hours in nitrogen, the catalyst composition had an MSA of 530 m$^2$/g of the molecular sieve.

Examples 2 to 4

The procedure of Example 1 was repeated but with varying amounts of phosphoric acid being added to the slurry of SAPO-34 and alumina binder, prior to the addition of the clay matrix. After addition of the phosphoric acid, the slurry was mixed at 700 RPM using the Yamato 4000D mixer for 10 minutes, and then mixed using the Silverson high-shear mixer at 6000 RPM for 3 minutes. The final catalyst precursor slurry had the same solids content (45 wt %) and the same relative proportions of SAPO-34, alumina binder and clay matrix (40 wt %, 10.6 wt % and 49.4 wt % respectively) as in Example 1 but, as will be seen from the data reported in Table 1 below, had a significantly lower viscosity than the equivalent slurry of Example 1.

After spray drying and calcination as in Example 1, the catalyst composition had the properties reported in Table 1 below.

TABLE 1

| Example | 2 | 3 | 4 |
|---|---|---|---|
| P content (as wt % P$_2$O$_5$) | 0.5 | 1.0 | 2.5 |
| Slurry Viscosity (cps) | 1390 | 1400 | 730 |
| Apparent Bulk Density (g/cc) | 0.82 | 0.8 | 0.87 |
| MSA (m$^2$/g of molecular sieve) | 506.2 | 510.2 | 520 |
| MSA after calcination at 760° C. for 3 hrs (m$^2$/g of molecular sieve) | 537.8 | 534.5 | 541.2 |
| ARI (wt %/hr) | 0.61 | 0.80 | 0.31 |

It will be seen from Table 1 that the addition of the phosphorus compound to the catalyst formulation of Example 2 increased the bulk density and decreased the rate of attrition of the final catalyst.

Example 5 (Comparative)

Conversion Process

The catalytic performance of the catalyst composition of Example 1 for conversion of methanol was conducted using a micro-reactor unit. Reaction conditions employed were a temperature of 425° C., a methanol partial pressure of 25 psig (273 kPag) and a WHSV based on the SAPO-34 in the catalyst of 318 hr$^{-1}$. The maximum first order rate constant for methanol conversion was found to be 314.8 sec$^{-1}$ and the selectivity to prime olefins (ethylene and propylene) was 66.0 wt %.

The catalytic performance of the catalyst composition of Example 1 for conversion of methanol was repeated after the catalyst had been treated for 18 hours at a temperature of 800° C. and a total pressure of 50 psig (446 kPag) in the presence of 0.1 g water/g of catalyst and 15 cc nitrogen/g of catalyst. Under the same conditions as used in the previous test, the maximum first order rate constant for methanol conversion was found to be 48.2 sec$^{-1}$ and the selectivity to prime olefins (ethylene and propylene) was 64.5 wt %. This represents a decrease in catalytic activity of 84.7%.

Example 6

Conversion Process

The catalytic performance of the catalyst composition of Example 4 (containing 2.5 wt % P$_2$O$_5$) for conversion of methanol was conducted using a micro-reactor unit. As in Example 5, the reaction conditions employed were a temperature of 425° C., a methanol partial pressure of 25 psig (273 kpag) and a WHSV based on the SAPO-34 in the catalyst of 318 hr$^{-1}$. The maximum first order rate constant for methanol conversion was found to be 257.2 sec$^{-1}$ and the selectivity to prime olefins (ethylene and propylene) was 59.6 wt %.

The catalytic performance of the catalyst composition of Example 4 for conversion of methanol was repeated after the catalyst had been treated for 18 hours at a temperature of 800° C. and a pressure of 50 psig (446 kPag) in the presence of 0.1 g water/g of catalyst and 15 cc nitrogen/g of catalyst. Under the same conditions as used in the previous test, the maximum first order rate constant for methanol conversion was found to be 208.8 sec$^{-1}$ and the selectivity to prime olefins (ethylene and propylene) was 62.5 wt %. Thus the catalyst of Example 4 exhibited a significant improvement in hydrothermal stability as compared with the catalyst of Example 1.

While the present invention has been described and illustrated by reference to particular embodiments, those of ordinary skill in the art will appreciate that the invention lends itself to variations not necessarily illustrated herein. For example, it is contemplated that the catalyst compositions described herein are useful in the inter-conversion of olefin(s), oxygenate to gasoline conversions reactions, maleic anhydride, phthalic anyhdride and acrylonitrile formation, vapor phase methanol synthesis, and various Fischer Tropsch reactions. It is also contemplated the catalyst compositions described herein are useful as absorbents, adsorbents, gas separators, detergents, water purifiers, and other various uses such as agriculture and horticulture. Additionally contemplated are catalyst compositions including more than one molecular sieve in combination. For this reason, then, reference should be made solely to the appended claims for purposes of determining the true scope of the present invention.

We claim:

1. A catalyst composition comprising:
   a molecular sieve having a framework including at least [AlO$_4$] and [PO$_4$] tetrahedral units,
   a binder and a matrix material, and
   at least one phosphorus compound separate from said molecular sieve;
   wherein said composition is formed from a substantially homogeneous catalyst precursor mixture comprising said molecular sieve, said binder, said matrix material and said phosphorus compound and to which said phosphorus compound and binder are added prior to addition of said matrix material during formulation of said catalyst precursor mixture,
   wherein said catalyst precursor mixture has a particle size distribution of at least 90 percent of solid particles having a diameter less than 20 μm; and
   wherein, after calcination at 760° C. for 3 hours, said catalyst composition has a microporous surface area in the range of from about 400 to 600 m$^2$/g-molecular sieve and further has a microporous surface area in excess of 20% of the microporous surface area of said molecular sieve after calcination at 650° C. in nitrogen for 2 hours.

2. The catalyst composition of claim 1 wherein, after calcination at 760° C. for 3 hours, said catalyst composition has a microporous surface area in excess of 50% of the microporous surface area of said molecular sieve after calcination at 650° C. in nitrogen for 2 hours.

3. The catalyst composition of claim 1 wherein, after calcination at 760° C. for 3 hours, said catalyst composition has a microporous surface area in excess of 100% of the microporous surface area of said molecular sieve after calcination at 650° C. in nitrogen for 2 hours.

4. The catalyst composition of claim 1 wherein said phosphorus compound is present in amount of between about 0.05 and about 15 wt %, expressed as $P_2O_5$, by weight of the catalyst composition.

5. The catalyst composition of claim 1 wherein said phosphorus compound is present in amount of between about 0.1 and about 10 wt %, expressed as $P_2O_5$, by weight of the catalyst composition.

6. The catalyst composition of claim 1 wherein said phosphorus compound is present in amount of between about 0.5 and about 6 wt %, expressed as $P_2O_5$, by weight of the catalyst composition.

7. The catalyst composition of claim 1 wherein said phosphorus compound is present in amount of between greater 1.0 and about 5 wt %, expressed as $P_2O_5$, by weight of the catalyst composition.

8. The catalyst composition of claim 1 and having an Attrition Rate Index (ARI), of less than 3 wt % per hour.

9. The catalyst composition of claim 1 and having an Attrition Rate Index (ARI), of less than 0.95 wt % per hour.

10. The catalyst composition of claim 1 and having an Attrition Rate Index (ARI), of about 0.05 to about 0.8 wt % per hour.

11. The catalyst composition of claim 1 wherein, after hydrothermal treatment at 800° C. for 18 hours at a water vapor pressure of 45 psig, said catalyst composition retains at least 15% of the methanol conversion activity of the untreated catalyst composition.

12. The catalyst composition of claim 1 and including a binder comprising alumina.

13. The catalyst composition of claim 12 and further including a matrix material comprising a clay.

14. The catalyst composition of claim 1 wherein the molecular sieve is selected from aluminophosphates, silicoaluminophosphates and metal-containing derivatives thereof.

15. The catalyst composition of claim 14 wherein the molecular sieve comprises a CHA framework-type molecular sieve.

16. The catalyst composition of claim 15 wherein the molecular sieve further comprises an AEI framework-type molecular sieve.

17. A catalyst composition comprising:
    a molecular sieve having a framework including at least [$AlO_4$] and [$PO_4$] tetrahedral units,
    a binder and a matrix material, and
    at least one phosphorus compound separate from said molecular sieve;
wherein said composition is formed from a substantially homogeneous catalyst precursor mixture comprising said molecular sieve, said binder, said matrix material and said phosphorus compound and to which said phosphorus compound and binder are added prior to addition of said matrix material during formulation of said catalyst precursor mixture,
wherein said catalyst precursor mixture has a particle size distribution of at least 90 percent of solid particles having a diameter less than 20 μm;
wherein, after calcination at 760° C. for 3 hours, said catalyst composition has a microporous surface area in the range of from about 400 to 600 $m^2$/g-molecular sieve; and
wherein, after hydrothermal treatment at 800° C. for 18 hours at a water vapor pressure of 45 psig, said catalyst composition retains at least 15% of the methanol conversion activity of the untreated catalyst composition.

18. The catalyst composition of claim 17 wherein, after hydrothermal treatment at 800° C. for 18 hours at a water vapor pressure of 45 psig, said catalyst composition retains at least 20% of the methanol conversion activity of the untreated catalyst composition.

19. The catalyst composition of claim 17 wherein, after hydrothermal treatment at 800° C. for 18 hours at a water vapor pressure of 45 psig, said catalyst composition retains at least 25% of the methanol conversion activity of the untreated catalyst composition.

20. The catalyst composition of claim 17 wherein said phosphorus compound is present in amount of between about 0.05 to about 15 wt %, expressed as $P_2O_5$, by weight of the catalyst composition.

21. The catalyst composition of claim 17 wherein said phosphorus compound is present in amount of between about 0.1 to about 10 wt %, expressed as $P_2O_5$, by weight of the catalyst composition.

22. The catalyst composition of claim 17 and having an Attrition Rate Index (ARI), of less than 0.95 wt % per hour.

23. The catalyst composition of claim 17 and including a binder comprising alumina.

24. The catalyst composition of claim 23 and further including a matrix material comprising a clay.

25. The catalyst composition of claim 17 wherein the molecular sieve is selected from aluminophosphates, silicoaluminophosphates and metal-containing derivatives thereof.

26. The catalyst composition of claim 25 wherein the molecular sieve comprises a CHA framework-type molecular sieve.

27. The catalyst composition of claim 26 wherein the molecular sieve further comprises an AEI framework-type molecular sieve.

* * * * *